US008715942B2

(12) United States Patent
Chapoteau et al.

(10) Patent No.: US 8,715,942 B2
(45) Date of Patent: May 6, 2014

(54) METHODS FOR THE DETECTION OF GLYCATED HEMOGLOBIN

(75) Inventors: Eddy Chapoteau, Brooklyn, NY (US); Richard Edwards, Cold Spring, NY (US); Chester Swirski, Yorktown, NY (US); Wolodymyr Zazulak, New Fairfield, CT (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 864 days.

(21) Appl. No.: 12/743,615

(22) PCT Filed: Nov. 18, 2008

(86) PCT No.: PCT/US2008/083847
§ 371 (c)(1),
(2), (4) Date: May 19, 2010

(87) PCT Pub. No.: WO2009/067421
PCT Pub. Date: May 28, 2009

(65) Prior Publication Data
US 2010/0273181 A1    Oct. 28, 2010

Related U.S. Application Data

(60) Provisional application No. 60/989,210, filed on Nov. 20, 2007.

(51) Int. Cl.
*G01N 33/53*    (2006.01)
(52) U.S. Cl.
CPC ..................................... *G01N 33/53* (2013.01)
USPC ........................... 435/7.1; 435/7.92; 436/501
(58) Field of Classification Search
None
See application file for complete search history.

(56) References Cited

U.S. PATENT DOCUMENTS

| | | | |
|---|---|---|---|
| 4,727,036 A * | 2/1988 | Knowles et al. | 530/387.9 |
| 4,847,209 A | 7/1989 | Lewis et al. | |
| 4,968,742 A | 11/1990 | Lewis et al. | |
| 6,043,043 A | 3/2000 | Yip | |
| 6,127,138 A * | 10/2000 | Ishimaru et al. | 435/23 |
| 6,790,665 B2 | 9/2004 | Yonehara et al. | |
| 7,153,666 B2 * | 12/2006 | Yuan et al. | 435/23 |
| 7,235,378 B2 * | 6/2007 | Yonehara | 435/14 |
| 2013/0078664 A1 * | 3/2013 | Yuan et al. | 435/28 |

FOREIGN PATENT DOCUMENTS

| | | | |
|---|---|---|---|
| JP | Hei 01-155268 A | 6/1989 | |
| JP | 2000-300294 A | 10/2000 | |
| JP | 2006-254918 A | 9/2006 | |
| WO | 2004/104203 A1 | 12/2004 | |

OTHER PUBLICATIONS

Tadashi Yoshimoto et al., "Proline-specific Endopetidase from *Flavobacterium*" The Journal of Biological Chemistry, May 25, 1980, vol. 255 No. 10, pp.4786-4-4592.
Vesper Hubert W,et al; "Assessment of microwave-assisted enzyme digestion by measuring glycated hemoglobin Ac by Mass Spectrometry", 2005, Rapid Communications in Mass Spectrometry, vol. 19 Nr. 19 pp. 2865-2870. XP002608481, ISSN 0951-4198, p. 2866, left-hand column paragraph 2, p. 2866, right hand column, last paragraph.
Metus Paolo et al., "Immunoturbidimetric Assay of Glycated Hemoglobin", 1999, Journal of Clinical Laboratory Analysis, vol. 13, Nr 1 pp. 5-8 XP002608482, ISSN 0887-8013, p. 5 right hand column, p. 6 left hand column.
Tiran Andreas et al, "Automated Determination of Glycated Hemoglobin: Comparative Evaluation of five Assay Systems" 1994, Journal of Clinical Laboratory Analysis, vol. 8 Nr. 3 pp. 128-134, XP002608483, ISSN 0887-8013, the whole document.
Bry, L., et al., "Effects of Hemoglobin variants and chemically modified derivatives on assays for glycohemoglobin," Clinical Chemistry, 2001, 47(2), 153-163.
"Hemoglobin A1c (HbA1c)," ADVIA IMS Methods Guide, 2004, 1-9.
Holownia, P., et al., "Adaptation of latex-enhanced assay for percent glycohemoglobin to a Dade Dimension analyzer," Clinical Chemistry, 1997, 43(1), 76-84.
Jeppsson, J.-O., et al., "Approved IFCC Reference Method for the measurement of HbA1c in Human Blood," Clin. Chem. Lab Med., 2002, 40(1), 78-89.
Konigsberg, W., et al., The Structure of Human Hemoglobin. VII. The digestion of the β Chain of human hemoglobin with pepsin,: Journal of Biological chemistry, 1963, 238,(6), 2028-2033.
Wolf, H.U., et al., "Alkaline haematin D-575, a new tool for the determination of haemoglobin as an alternative to the cyanhaemiglobin method. II.Standardisation of the method using pure chlorohaemin," Clin Chim Acta, 1984, 136, 95-104.
Sakurabayshi, I., et al., "New Enzymatic Assay for Glycohemoglobin," Clinical Chemistry, 2003, 49(2), 269-274.
Zander, R., et al., "Alkaline haematin D-575, a new tool for the determination of haemoglobin as an alternative to the cyanhaemiglobin method. I, Description of the method," Clin Chim Acta, 1984, 136, 83-93.
Japanese Office Action dated Jul. 23, 2013 for Japanese Application No. 2010-535022 (5 pages).

* cited by examiner

*Primary Examiner* — Gary W Counts
(74) *Attorney, Agent, or Firm* — Woodcock Washburn LLP; Kevin Stein (57) ABSTRACT

Provided herein are methods for detecting glycated hemoglobin in, for example, human whole blood, that are not affected by the presence of variation in amino acid sequence that can exist in hemoglobin β chains. The methods detect all glycated hemoglobin in a sample, regardless of the form of the hemoglobin that has been glycated, and thus detect glycated human Hemoglobin A, Hemoglobin S, and Hemoglobin C.

24 Claims, 10 Drawing Sheets

SEQUENCE LISTING

<160> NUMBER OF SEQ ID NOS: 4

<210> SEQ ID NO 1
<211> LENGTH: 18
<212> TYPE: PRT
<213> ORGANISM: Homo sapiens

```
-continued

<400> SEQUENCE: 1

Val His Leu Thr Pro Glu Glu Lys Ser Ala Val Thr Ala Leu Trp Gly
1               5                   10                  15

Lys Val

<210> SEQ ID NO 2
<211> LENGTH: 18
<212> TYPE: PRT
<213> ORGANISM: Homo sapiens

<400> SEQUENCE: 2

Val His Leu Thr Pro Lys Glu Lys Ser Ala Val Thr Ala Leu Trp Gly
1               5                   10                  15

Lys Val

<210> SEQ ID NO 3
<211> LENGTH: 18
<212> TYPE: PRT
<213> ORGANISM: Homo sapiens

<400> SEQUENCE: 3

Val His Leu Thr Pro Val Glu Lys Ser Ala Val Thr Ala Leu Trp Gly
1               5                   10                  15

Lys Val

<210> SEQ ID NO 4
<211> LENGTH: 6
<212> TYPE: PRT
<213> ORGANISM: Homo sapiens

<400> SEQUENCE: 4

Val His Leu Thr Tyr Cys
1               5
```

METHODS FOR THE DETECTION OF GLYCATED HEMOGLOBIN

This application is the national stage of International Appl. No. PCT/US08/83847, filed Nov. 18, 2008, which claims the benefit of U.S. Provisional Appl. No. 60/989,210, filed Nov. 20, 2007.

FIELD OF THE INVENTION

Particular aspects of the present invention relate to methods for detecting glycated human hemoglobin in, for example, human whole blood, that are not affected by the presence of hemoglobin variants in the blood.

BACKGROUND OF THE INVENTION

Hemoglobin present in red blood cells can be glycated by the non-enzymatic addition of a glucose molecule to the amino terminus of the β-chain of the hemoglobin. Once a hemoglobin molecule is glycated, it remains glycated, and an accumulation of glycated hemoglobin within a red cell reflects the average level of glucose to which the cell has been exposed during its life cycle. The level of glycated hemoglobin present in an individual's blood is thus proportional to the level of glucose in the blood, and is an indicator of the individual's mean daily blood glucose concentration over the previous four weeks to three months.

Numerous methods exist for determining the level of glycated hemoglobin in human blood, most of which involve calculating the relative amount of glycated hemoglobin A (HbA1c) present in the blood, due to the fact that hemoglobin A (HbA) is the major form of hemoglobin present in human blood. Techniques such as high performance liquid chromatography and immunoaffinity selection are used in such methods, which take advantage of physical and/or chemical properties of glycated hemoglobin A that distinguish it from other forms of hemoglobin present in the blood.

Variant forms of hemoglobin exist, however, such as hemoglobin S (HbS) and hemoglobin C (HbC), which differ from hemoglobin A at the amino acid residue at position six of the hemoglobin β-chain. The hemoglobin S and hemoglobin C forms of hemoglobin can be glycated, and glycated hemoglobin S and hemoglobin C have been shown to interfere with most of the current methods for quantitating glycated human hemoglobin, causing up to a 40% elevation in the results. A need therefore exists for methods for detecting glycated human hemoglobin that are not subject to interference caused by hemoglobin variants.

SUMMARY OF THE INVENTION

In certain embodiments, the invention relates to methods for detecting glycated human hemoglobin that comprise contacting a sample to be tested for glycated human hemoglobin with an endopeptidase, contacting the endopeptidase-treated sample with proline-specific endopeptidase, and detecting glycated β-chain amino-terminal pentapeptide of human hemoglobin.

In other embodiments, the invention relates to methods for detecting glycated human hemoglobin that comprise contacting a sample to be tested for glycated human hemoglobin with an endopeptidase either simultaneously with, prior to, or following contacting the sample with an agglutinator reagent, contacting the endopeptidase and agglutinator reagent-treated sample with proline-specific endopeptidase, and detecting glycated β-chain amino-terminal pentapeptide of human hemoglobin with an agglutination inhibition immunoassay.

BRIEF DESCRIPTION OF THE DRAWINGS

FIG. 8 depicts a correlation slope in which the percentage of glycated hemoglobin determined to be present in human whole blood samples containing hemoglobin S and hemoglobin C that were reacted with an agglutinator reagent and 0.43 U/mL proline-specific endopeptidase using an ADVIA®

1650 instrument is plotted against the percentage of glycated hemoglobin present in the samples determined using the DCA® 2000 HbA1c assay.

DETAILED DESCRIPTION OF ILLUSTRATIVE EMBODIMENTS

Particular aspects of the present invention relate to methods for detecting glycated hemoglobin present in human blood that are not affected by the variation in amino acid sequence that can exist in hemoglobin β chains. The methods detect all glycated hemoglobin in a sample, regardless of the form of the hemoglobin that has been glycated, and thus detect glycated hemoglobin A, hemoglobin S, and hemoglobin C.

Hemoglobin S and hemoglobin C contain a point mutation at position 6 of the human hemoglobin p chain. The glutamic acid residue at position six of the hemoglobin A β chain is replaced with a lysine residue in hemoglobin C and with a valine residue in hemoglobin S. The glycated amino terminal 18 amino acids of the human hemoglobin A, hemoglobin S, and hemoglobin C β chains are shown below:

```
HbA:
                                         (SEQ ID NO: 1)
Glucose-val-his-leu-thr-pro-glu-glu-lys-ser-alaval-thr-ala-leu-trp-gly-lys-val HbC:
                                         (SEQ ID NO: 2)
Glucose-val-his-leu-thr-pro-lys-glu-lys-ser-alaval-thr-ala-leu-trp-gly-lys-val HbS:
                                         (SEQ ID NO: 3)
Glucose-val-his-leu-thr-pro-val-glu-lys-ser-alaval-thr-ala-leu-trp-gly-lys-val
```

Proline specific endopeptidase (PSE) selectively cleaves at the carboxy side of the proline residue at position 5 of the human hemoglobin β chain. Digestion of samples containing hemoglobin A, hemoglobin S, and hemoglobin C with proline-specific endopeptidase thus yields the same glycated pentapeptide for each of hemoglobin A, hemoglobin S, and hemoglobin C.

Certain embodiments of the present invention relate to methods that include digesting endopeptidase-treated human hemoglobin-containing samples with proline specific endopeptidase to liberate the glycated or unglycated amino-terminal pentapeptide of the human hemoglobin β chain. The level of glycated pentapeptide in the samples can then be quantitated to provide an indication of the amount of glycated hemoglobin present in the samples.

As used herein, the terms "detect," "detecting," and all variations thereof refer to any method used to quantitatively determine the presence of glycated human hemoglobin or of the amino-terminal pentapeptide of glycated human hemoglobin present in a sample regardless of the amount of the glycated human hemoglobin or of the amino-terminal pentapeptide of glycated human hemoglobin present in the sample and regardless of the form of the hemoglobin present in the sample and regardless of the form of the hemoglobin in the sample from which the peptide As used herein, the term "glycated human hemoglobin" refers to any form of human hemoglobin to which a glucose molecule has been bound to the amino terminus of the β-chain of the hemoglobin without the action of an enzyme. The term "glycated β-chain amino-terminal pentapeptide of human hemoglobin" refers to the amino-terminal pentapeptide of the β-chain of any form of human hemoglobin to which a glucose molecule has been bound to the amino-terminus of the pentapeptide without the action of an enzyme.

As used herein, the terms "contacting," "contact," and all variations thereof, refer to any means that directly or indirectly cause placement together of moieties or components, such that the moieties or components come into physical contact with each other. Contacting thus includes physical acts such as placing the moieties or components together in a container, combining the moieties or components, or mixing the moieties or components.

As used herein, the term "endopeptidase" refers to any enzyme that hydrolyzes a peptide bond in a peptide, polypeptide or protein.

As used herein, the term "acid endopeptidase" refers to any enzyme that hydrolyzes a peptide bond in a peptide, polypeptide or protein in an acidic environment.

As used herein, the terms "mixing," "mix," "adding," and "add," and all variations thereof, refer to any means that directly or indirectly cause placement together of moieties or components, such that the moieties or components come into close proximity to each other. The terms include acts such as placing the moieties or components together in a container, combining the moieties or components, contacting the moieties or components, or stirring, vortexing, or agitating the moieties or components together. The term "mixture" refers to moieties or components that have been placed together in close proximity.

Particular aspects of the invention relate to methods for detecting glycated human hemoglobin that comprise contacting a sample to be tested for glycated human hemoglobin with an endopeptidase, contacting the endopeptidase-treated sample with proline-specific endopeptidase, and detecting glycated β-chain amino-terminal pentapeptide of human hemoglobin present in the sample.

In preferred embodiments of the invention, the sample is human whole blood.

In certain embodiments of the invention, the percentage of glycated human hemoglobin in the sample is determined. In such methods, the concentration of glycated human hemoglobin in the sample is determined and the total hemoglobin concentration, which includes both glycated human hemoglobin in the sample is calculated by dividing the concentration of the glycated hemoglobin by the concentration of the total hemoglobin.

The total hemoglobin concentration in the sample can be determined using methods familiar to those skilled in the art, including, for example, an assay based on the conversion of all hemoglobin derivatives into alkaline hematin upon treatment with an alkaline solution of a nonionic detergent, as described in Wolf, H. U., et al., *Clin Chim Acta*, 1984, 136, 95-104 and Zander R., et al., *Clin Chim Acta*, 1984, 136, 83-93, incorporated herein by reference in their entireties.

Alkaline hematin has a defined absorption spectrum at 600 nm, and the hematin content can be measured by determining absorption at 600 nm.

Any endopeptidase can be used to initially digest the human hemoglobin present in a sample before digestion with proline-specific endopeptidase. The endopeptidase digestion can be performed manually or can be performed automatically on any chemistry system capable of sample dilution.

In particular embodiments of the invention, the endopeptidase is an acid endopeptidase. In preferred embodiments of the invention, the acid endopeptidase is pepsin, aspergillopepsin II, cathepsin D, saccharopepsin, mucorpepsin, chymosin, gastricsin, or physirolisin. In particularly preferred embodiments, the acid endopeptidase is pepsin. In certain aspects of the invention, the samples are digested with about 5 U/mL to about 10,000 U/mL pepsin. In preferred embodiments, the samples are digested with about 4,800 U/mL to about 8,600 U/mL pepsin. In particularly preferred embodiments, the samples are digested with about 6,000 U/mL to about 7,000 U/mL pepsin. In particular embodiments of the invention, the pepsin digestion is performed at a pH in the range of about 1.0 to about 5.0. In preferred embodiments of the invention, the pepsin digestion is performed at a pH in the range of about 2.0 to about 4.0. In particularly preferred embodiments of the invention, the pepsin digestion is performed at a pH in the range of about 2.3 to about 2.5.

In certain embodiments of the invention, following endopeptidase digestion, samples are digested with proline-specific endopeptidase. In particular embodiments, such samples are treated with about 0.1 U/mL to about 30 U/mL proline-specific endopeptidase. In preferred embodiments, such samples are treated with about 0.3 U/mL to about 5.0 U/mL proline-specific endopeptidase. In particularly preferred embodiments, such samples are treated with about 0.5 U/mL to about 0.8 U/mL proline-specific endopeptidase. In particular embodiments of the invention, such proline-specific endopeptidase digestions are performed at a pH in the range of about 5.0 to about 9.0. In preferred embodiments of the invention, such proline-specific endopeptidase digestions are performed at a pH in the range of about 6.0 to about 8.0. In particularly preferred embodiments of the invention, such proline-specific endopeptidase digestions are performed at a pH in the range of about 6.9 to about 7.1.

The glycated β-chain amino-terminal pentapeptide of human hemoglobin liberated following endopeptidase and proline-specific endopeptidase digestion can be detected with any method, including, for example, methods that comprise the use of high performance liquid chromatography or that comprises the binding of at least one antibody, whether polyclonal or monoclonal, to the glycated pentapeptide.

In preferred embodiments of the invention, the glycated β-chain amino-terminal pentapeptide of human hemoglobin is detected with an agglutination inhibition immunoassay, as described, for example, in U.S. Pat. No. 4,847,209, incorporated herein by reference in its entirety. In particular examples of such assays, samples containing the glycated β-chain amino-terminal pentapeptide of human hemoglobin are mixed with an agglutinator reagent, such as, for example, glycated val-his-leu-thr-tyr-cys (SEQ ID NO: 4) sexapeptide conjugated to polyaspartamide. Samples are also mixed with an antibody. In preferred embodiments of the invention, the antibody specifically binds to both the glycated β-chain amino-terminal pentapeptide of human hemoglobin and the agglutinator reagent. In particular aspects of the invention, at least one antibody molecule is bound to one or more latex particles. Preferred antibodies include, for example, latex-coated mouse monoclonal anti-HbA1c antibody.

In such agglutination inhibition immunoassays, the β-chain amino-terminal glycated pentapeptide of human hemoglobin in a sample competes with the agglutinator reagent for antibody binding sites and slows the rate of agglutination, which occurs when the agglutinator reagent binds the latex-coated antibody. The more β-chain amino-terminal glycated pentapeptide of human hemoglobin present in the sample, the slower the rate of agglutination. The rate of agglutination thus provides an indication of the concentration of the β-chain amino-terminal glycated pentapeptide of human hemoglobin present in the sample.

The endopeptidase digestion, proline-specific endopeptidase digestion, and agglutination inhibition immunoassay can be performed in various ways. For example, in certain embodiments of the invention, the samples are first digested with an endopeptidase and the endopeptidase-treated samples are then reacted with proline-specific endopeptidase, followed by contacting the sample with an agglutinator reagent, followed by contacting the samples with an antibody. In other embodiments of the invention, the samples are first digested with an endopeptidase and the endopeptidase-treated samples are then contacted with a mixture of proline-specific endopeptidase and an agglutinator reagent, followed by contacting the samples with an antibody. In still further embodiments of the invention, the samples are first digested with an endopeptidase and the endopeptidase-treated samples are then contacted with an agglutinator reagent, followed by contacting the samples with proline-specific endopeptidase, followed by contacting the samples with an antibody.

Particular aspects of the invention thus relate to methods that comprise contacting samples with an endopeptidase and contacting the endopeptidase-treated samples with proline specific endopeptidase either simultaneously with, prior to, or following contacting the sample with an agglutinator reagent.

In preferred embodiments of the invention, the endopeptidase-treated sample is contacted with a mixture of proline specific endopeptidase and the agglutinator reagent. In particular examples of such embodiments, the mixture of proline specific endopeptidase and the agglutinator reagent comprises about 0.1 g/dL to about 5.0 g/dL bovine serum albumin and about 0.5 mmol/L to about 10.0 mmol/L ethylenediamine tetraacetic acid and has a pH in the range of about 6.0 to about 8.0. In preferred examples of such embodiments, the mixture of proline specific endopeptidase and the agglutinator reagent comprises about 1.0 g/dL to about 2.0 g/dL bovine serum albumin and about 1.0 mmol/L to about 5.0 mmol/L ethylenediamine tetraacetic acid and has a pH in the range of about 6.0 to about 8.0. In particularly preferred examples of such embodiments, the mixture of proline specific endopeptidase and the agglutinator reagent comprises about 1.4 g/dL to about 1.6 g/dL bovine serum albumin and about 2.9 mmol/L to about 3.1 mmol/L ethylenediamine tetraacetic acid and has a pH in the range of about 6.0 to about 8.0.

Particular embodiments of the invention relate to methods for detecting glycated human hemoglobin in which a sample is contacted with an endopeptidase and with an agglutinator reagent before contacting the sample with proline-specific endopeptidase. If the sample in such methods is human whole blood, the sample may, in some instances, be initially diluted with, for example, saline.

Particular aspects of the invention thus relate to methods that comprise contacting a sample with the mixture of an endopeptidase and an agglutinator reagent followed by contacting the sample with proline-specific endopeptidase, which is followed by contacting the sample with an antibody. Other embodiments of the invention relate to methods that comprise contacting a sample with a mixture of an endopeptidase and an agglutinator reagent, followed by contacting the sample with a mixture of proline-specific endopeptidase and an antibody. Further embodiments of the invention relate to methods that comprise contacting a sample with an agglutinator reagent followed by contacting the sample with pepsin, followed by contacting the sample with proline-specific endopeptidase, followed by contacting the sample with an antibody. Additional aspects of the invention relate to methods that comprise contacting a sample with an agglutinator reagent followed by contacting the sample with pepsin, followed by contacting the sample with a mixture of proline-specific endopeptidase and an antibody. Other aspects of the invention relate to methods that comprise contacting a sample with pepsin followed by contacting the sample with an agglutinator reagent, followed by contacting the sample with proline-specific endopeptidase, followed by contacting the sample with an antibody. Certain additional embodiments of the invention relate to methods that comprise contacting a sample with pepsin followed by contacting the sample with an agglutinator reagent, followed by contacting the sample with a mixture of proline-specific endopeptidase and an antibody.

Aspects of the invention thus relate to methods for detecting glycated human hemoglobin that comprise contacting a sample to be tested for glycated human hemoglobin with an endopeptidase either simultaneously with, prior to, or following contacting the sample with an agglutinator reagent, contacting the endopeptidase and agglutinator reagent-treated sample with proline-specific endopeptidase, and detecting glycated β-chain amino-terminal pentapeptide of human hemoglobin with an agglutination inhibition immunoassay. In preferred embodiments of such methods, the sample is contacted with a mixture of pepsin and the agglutinator reagent, which preferably comprises about 3 U/mL to about 100 U/mL pepsin and has a pH in the range of about 1.0 to about 4.0.

Further aspects of the invention relate to methods for detecting glycated human hemoglobin that comprise contacting a sample to be tested for glycated human hemoglobin with an endopeptidase either simultaneously with, prior to, or following contacting the sample with an agglutinator reagent, contacting the endopeptidase and agglutinator reagent-treated sample with proline-specific endopeptidase either simultaneously with or before contacting the sample with an antibody that specifically binds to both glycated β-chain amino-terminal pentapeptide of pentapeptide of human hemoglobin with an agglutination inhibition immunoassay. In preferred embodiments of such methods, the endopeptidase and agglutinator reagent-treated sample are contacted with a mixture of proline specific endopeptidase and the antibody, which preferably comprises about 2.0 U/mL to about 30.0 U/mL proline specific endopeptidase and has a pH in the range of about 7.0 to about 8.0.

The following examples are illustrative of certain embodiments of the invention and should not be considered to limit the scope of the invention.

Example 1

Digestion of Human Whole Blood Samples with Pepsin and Proline-Specific Endopeptidase 7.5 μL of DCA N (Normal control, DCA® 2000 Analyzer reagent kit (Siemens Medical Solutions Diagnostics)) or DCA AB (Abnormal control, DCA® 2000 Analyzer reagent kit (Siemens Medical Solutions Diagnostics)) were incubated at room temperature for 20 minutes with 150 μL Sample Denaturant Reagent (ADVIA® HbA1c reagent kit (Siemens Medical Solutions Diagnostics)) containing 250 U/mL of pepsin. 150 μL proline-specific endopeptidase (30 U/mL) in 0.1 mol/L phosphate buffer, pH 7.0, was added to half the pepsin-treated samples, and the proline-specific endopeptidase-treated samples were incubated for 30 minutes at room temperature. The remaining pepsin-treated samples were not treated with proline-specific endopeptidase, and 150 μL 0.1 mol/L phosphate buffer, pH 7.0, was added to those samples.

All samples were then tested in an agglutination inhibition immunoassay on an ADVIA® 1650 instrument by adding the samples to a mixture of latex coated with mouse monoclonal anti-HbA1c antibody (ADVIA® HbA1c reagent kit, R1 (Siemens Medical Solutions Diagnostics)) followed by the addition of the β-chain amino-terminal glycated sexapeptide of human hemoglobin conjugated to polyaspartamide (agglutinator reagent, ADVIA® HbA1c reagent kit, R2 (Siemens Medical Solutions Diagnostics)). The β-chain amino-terminal glycated pentapeptide of human hemoglobin in the sample competes with the agglutinator reagent for antibody binding sites and slows the rate of agglutination, which occurs when the agglutinator reagent binds the latex-coated antibody. The more β-chain amino-terminal glycated pentapeptide of human hemoglobin in the sample, the slower the rate of agglutination. The reaction was monitored at 694 nm and the difference in agglutination rates between the treated samples and a saline blank was determined. The results of the experiments are listed in Table 1 below and indicate that after treatment with pepsin, addition of proline-specific endopeptidase results in higher inhibition of agglutination, demonstrating that the β-chain terminal glycated pentapeptide of hemoglobin is released.

TABLE 1

| Sample | 20 min Pepsin | 20 min Pepsin + 30 min PSE (30 U/mL) |
|---|---|---|
| DCA N | −0.13856 | −0.17681 |
| DCA AB | −0.19191 | −0.21345 |

Example 2

Formulation of a Proline-Specific Edopeptidase-Containing Agglutinator Reagent

Conditions for the stable formulation of a reagent containing the agglutinator used in Example 1 (β-chain amino-terminal glycated sexapeptide of human hemoglobin conjugated to polyaspartamide) and proline-specific endopeptidase at pH 7.0 were determined.

Figure 1:
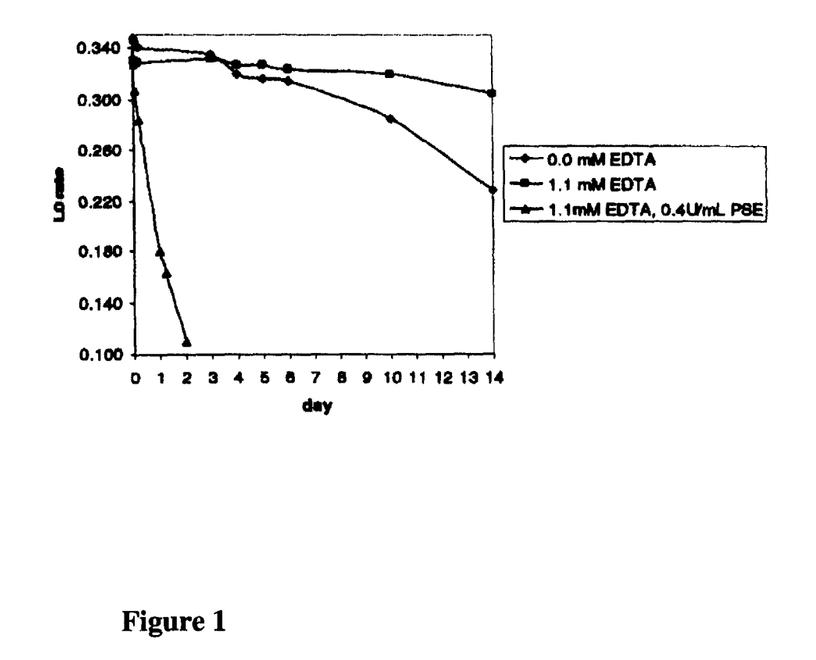
FIG. 1 depicts the rate of agglutination of latex coated with mouse monoclonal anti-HbA1c antibody caused by various formulations of an agglutinator reagent (polyaspartamide-conjugated β-chain amino-terminal glycated sexapeptide of human hemoglobin) over a period of 14 days. The formulations contained the agglutinator reagent without both ethylenediamine tetraacetic acid (EDTA) and proline-specific endopeptidase, with EDTA only, and with both EDTA and proline-specific endopeptidase.

Solutions of the agglutinator (approximately 1.5.mu.g/mL) containing 0.02 mol/L morpholino-propane-sulfonic acid (MOPS), 0.05% NaN.sub.3, and 0.2% TWEEN®-detergent, pH 7 were prepared either without ethylenediamine tetraacetic acid (EDTA) and 0.4 U/mL proline-specific endopeptidase, with 1.1 mmol/L EDTA, or with both 1.1 mmol/L EDTA and 0.4 U/mL proline-specific endopeptidase. The ability of the agglutinator in the various formulations to cause agglutination of latex coated with mouse monoclonal anti-HbA1c antibody over a period of 14 days was then determined to assess the stability of the agglutinator over time. Samples were tested in an agglutination inhibition immunoassay on an ADVIA® 1650 instrument by first adding the samples to the agglutinator reagent described above (R1) and then adding latex coated with mouse monoclonal anti-HbA1c antibody (ADVIA® HbA1c reagent kit, (Siemens Medical Solutions Diagnostics)) to the samples. The β-chain amino-terminal glycated pentapeptide of human hemoglobin in the samples compete with the agglutinator reagent for antibody binding sites and slows the rate of agglutination, which occurs when the agglutinator reagent binds the latex-coated antibody. The more β-chain amino-terminal glycated pentapeptide of human hemoglobin in the samples, the slower the rate of agglutination. The reactions were monitored at 694 nm and the rates of agglutination were determined. FIG. 1 illustrates that the agglutinator was the most stable in the presence of EDTA only and was the least stable in the presence of both EDTA and proline-specific endopeptidase.

Figure 2:
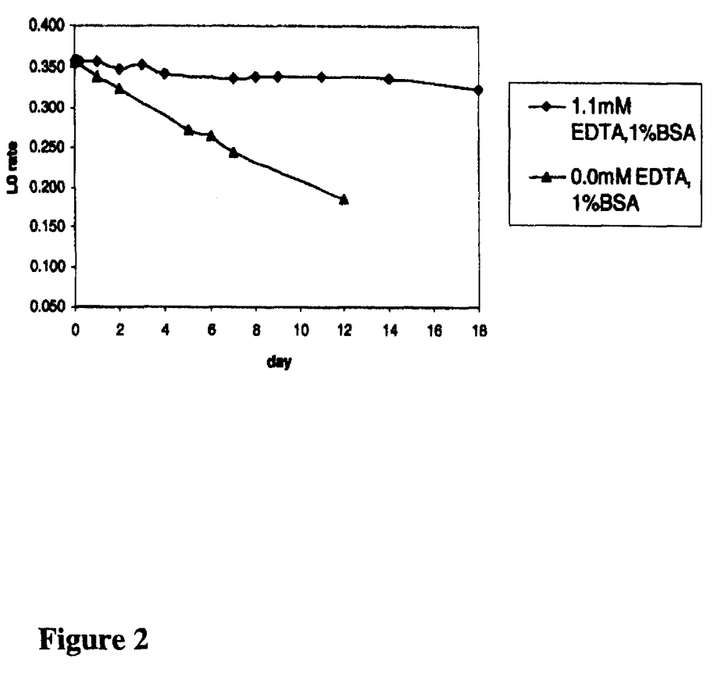
FIG. 2 depicts the rate of agglutination of latex coated with mouse monoclonal anti-HbA1c antibody caused by various formulations of an agglutinator reagent (polyaspartamide-conjugated β-chain amino-terminal glycated sexapeptide of human hemoglobin) over a period of 18 days. The formulations contained the agglutinator reagent and proline-specific endopeptidase with both EDTA and BSA, or with BSA only.
Figure 3:
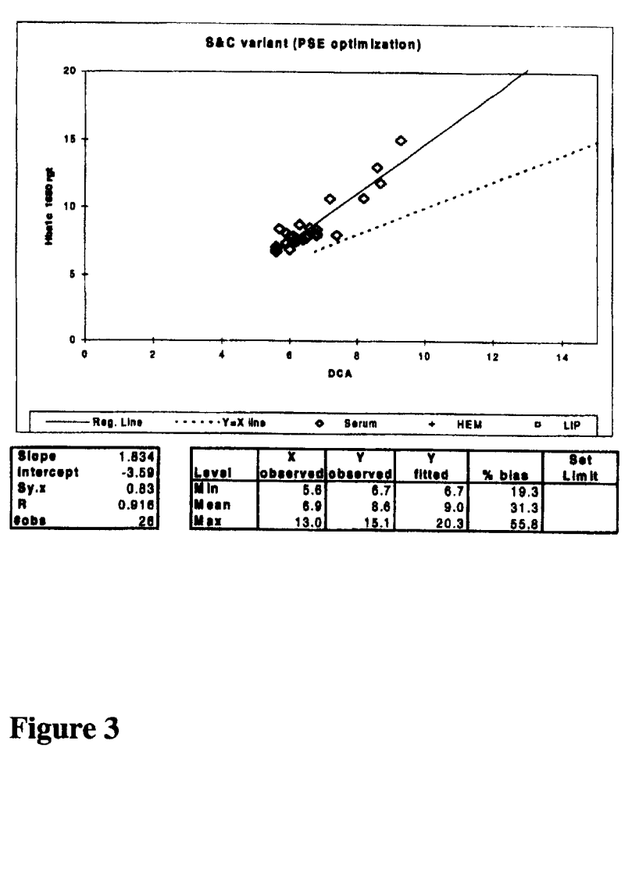
FIG. 3 depicts a correlation slope in which the percentage of glycated hemoglobin present in human whole blood samples containing hemoglobin S and hemoglobin C calculated using the ADVIA® 1650 HbA1c method is plotted against the percentage of glycated hemoglobin present in the samples calculated using the DCA® 2000 HbA1c assay.
Figure 4:
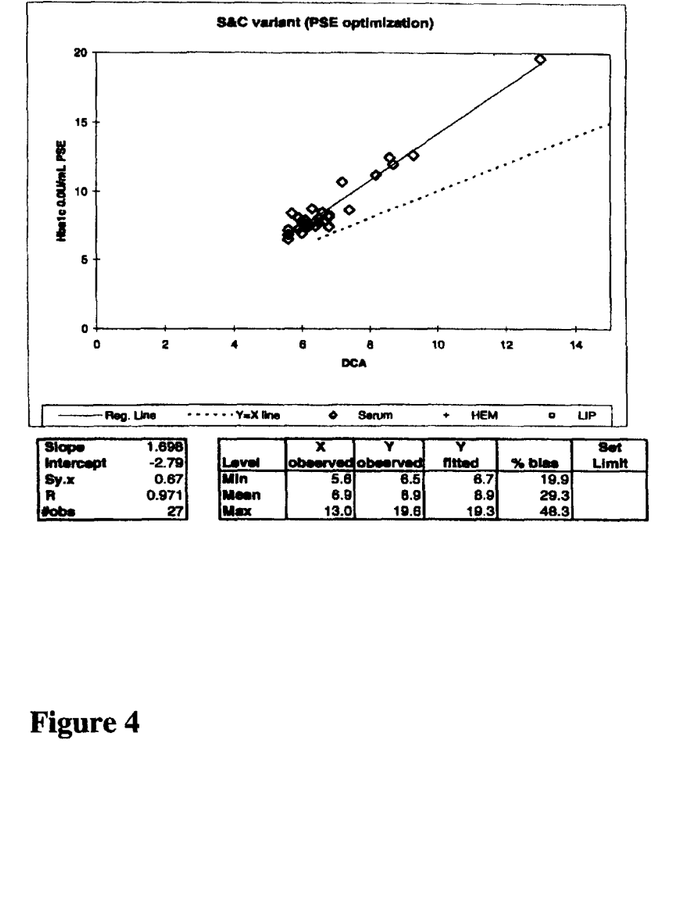
FIG. 4 depicts a correlation slope in which the percentage of glycated hemoglobin determined to be present in human whole blood samples containing hemoglobin S and hemoglobin C that were reacted with an agglutinator reagent and 0.0 U/mL proline-specific endopeptidase using an ADVIA® 1650 instrument is plotted against the percentage of glycated hemoglobin present in the samples determined using the DCA® 2000 HbA1c assay.
Figure 5:
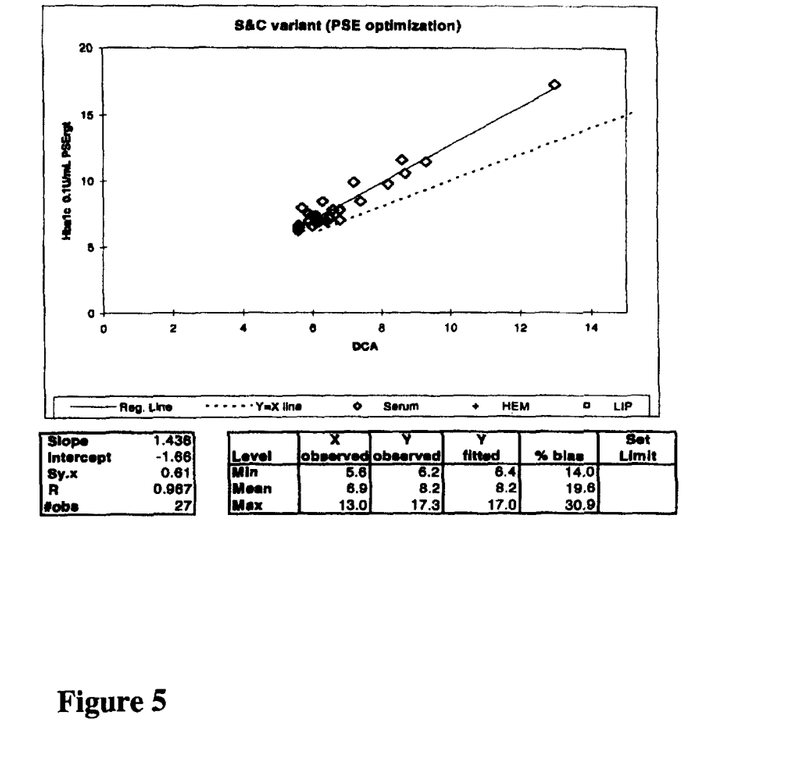
FIG. 5 depicts a correlation slope in which the percentage of glycated hemoglobin determined to be present in human whole blood samples containing hemoglobin S and hemoglobin C that were reacted with an agglutinator reagent and 0.1 U/mL proline-specific endopeptidase using an ADVIA® 1650 instrument is plotted against the percentage of glycated hemoglobin present in the samples determined using the DCA® 2000 HbA1c assay.
Figure 6:
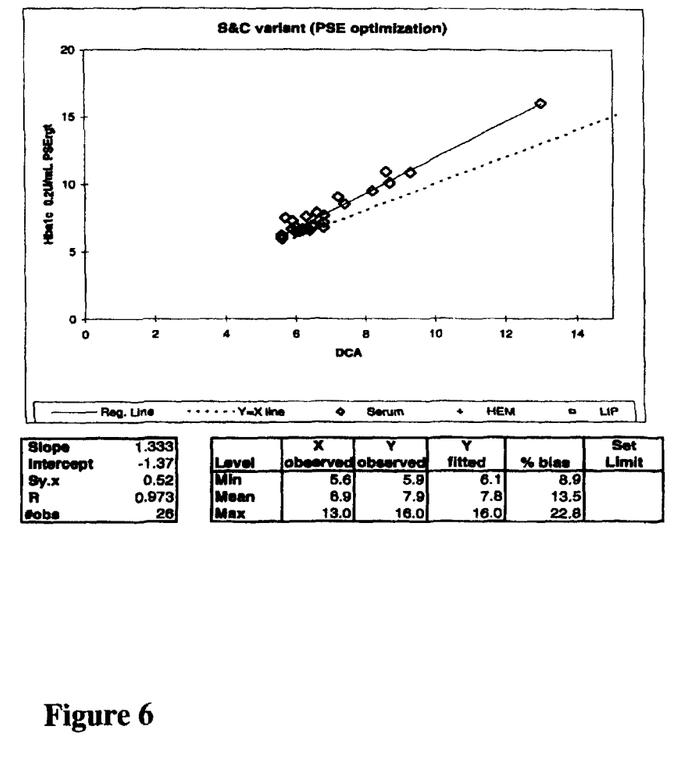
FIG. 6 depicts a correlation slope in which the percentage of glycated hemoglobin determined to be present in human whole blood samples containing hemoglobin S and hemoglobin C that were reacted with an agglutinator reagent and 0.2 U/mL proline-specific endopeptidase using an ADVIA® 1650 instrument is plotted against the percentage of glycated hemoglobin present in the samples determined using the DCA® 2000 HbA1c assay.
Figure 7:
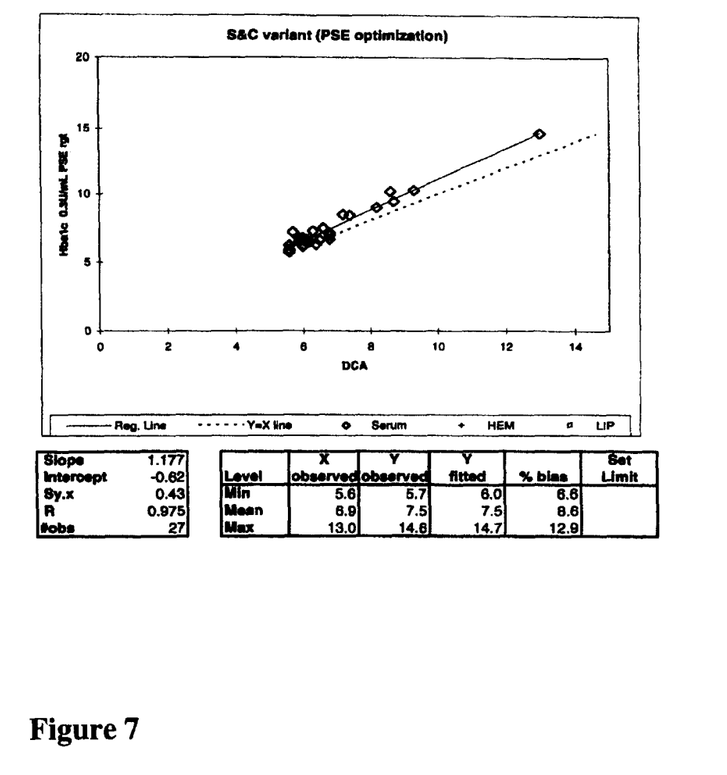
FIG. 7 depicts a correlation slope in which the percentage of glycated hemoglobin determined to be present in human whole blood samples containing hemoglobin S and hemoglobin C that were reacted with an agglutinator reagent and 0.33 U/mL proline-specific endopeptidase using an ADVIA® 1650 instrument is plotted against the percentage of glycated hemoglobin present in the samples determined using the DCA® 2000 HbA1c assay.
Figure 8:
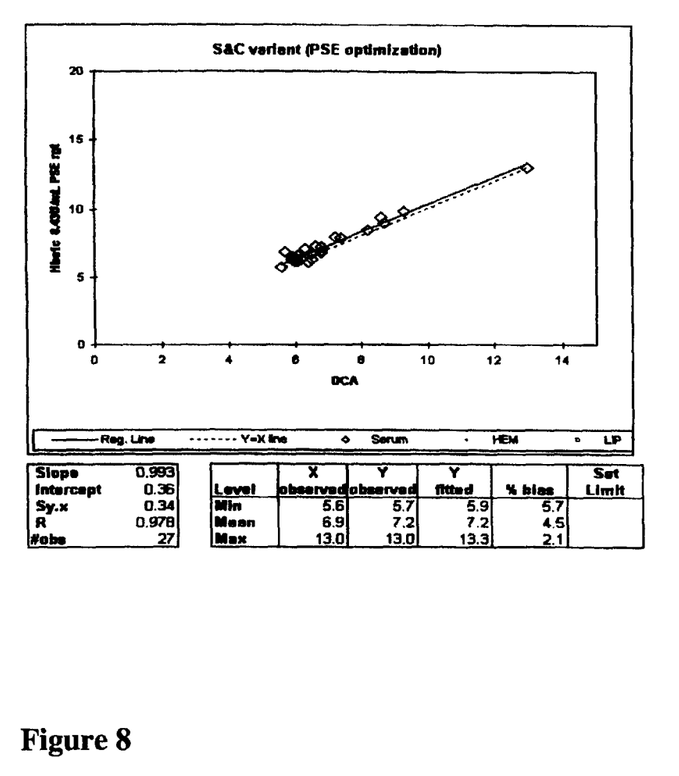
Figure 9:
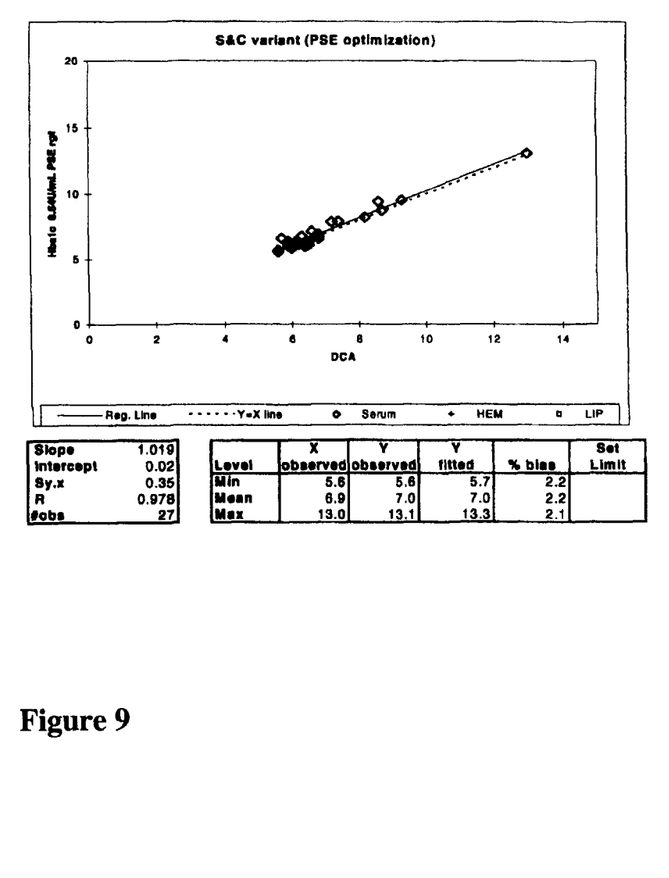
FIG. 9 depicts a correlation slope in which the percentage of glycated hemoglobin determined to be present in human whole blood samples containing hemoglobin S and hemoglobin C that were reacted with an agglutinator reagent and 0.54 U/mL proline-specific endopeptidase using an ADVIA® 1650 instrument is plotted against the percentage of glycated hemoglobin present in the samples determined using the DCA® 2000 HbA1c assay.

Additional solutions of the agglutinator (approximately 1.5 μg/mL) containing 0.4 U/mL proline-specific endopeptidase, 0.02 mol/L morpholino-propane-sulfonic acid (MOPS), 0.05% $NaN_3$, and 0.2% TWEEN®-20 detergent, pH 7 were prepared with both 1.1 mmol/L EDTA and 1% BSA or with only 1% BSA. The ability of the agglutinator in the various formulations to cause agglutination of latex coated with mouse monoclonal anti-HbA1c antibody over time was again determined. FIG. 2 illustrates that the agglutinator in the presence of proline-specific endopeptidase was more stable in solutions containing both bovine serum albumin (BSA) and EDTA than it was in solutions containing BSA only. The data provided in FIGS. 1 and 2 indicate that EDTA and BSA act synergistically to stabilize proline-specific endopeptidase-containing agglutinator reagent solutions.

Example 3

Determination of Pepsin Digestion Conditions

2 μL samples of lyophilized human whole blood containing various concentrations of HbA1c (Whole Blood HbA1c Calibrators, Aalto Scientific) were manually digested with 148 μL of 250 U/mL pepsin (Sample Denaturant Reagent (ADVIA® HbA1c reagent kit (Siemens Medical Solutions Diagnostics)) for 10 minutes, were digested for nine seconds with approximately 6000 U/mL pepsin in a 0.02 mmol/L citrate, 0.2% Triton X100 pH 2.4 solution in an automated fashion, or were digested for ten minutes with approximately 6000 U/mL pepsin in a 0.02 mmol/L citrate, 0.2% Triton X100 pH 2.4 solution in an automated fashion. The samples were then assessed in an agglutination inhibition immunoassay on an ADVIA® 1650 instrument as described in Example 2 where R1 was the agglutinator reagent containing 0.4 U/mL proline-specific endopeptidase. The lack of change among the agglutination rates listed for the different denaturing conditions for each respective sample in Table 2 below indicates that 9 seconds is sufficient for the pepsin denaturant containing approximately 6000 U/mL to digest hemoglobin.

TABLE 2

| Sample conc (μmol/L) HbA1c | Manual 10 min with sample denaturant ~250 U/mL pepsin | Automated 9 sec with ~6000 U/mL pepsin | Automated 10 min with ~6000 U/mL pepsin |
|---|---|---|---|
| | Agglutination rate | | |
| 0.00 | 0.27170 | 0.27137 | 0.27137 |
| 2.37 | 0.11992 | 0.11749 | 0.11868 |

TABLE 2-continued

| Sample conc (μmol/L) HbA1c | Manual 10 min with sample denaturant ~250 U/mL pepsin | Automated 9 sec with ~6000 U/mL pepsin | Automated 10 min with ~6000 U/mL pepsin |
|---|---|---|---|
| | Agglutination rate | | |
| 3.79 | 0.06581 | 0.06694 | 0.06621 |
| 4.75 | 0.04172 | 0.04162 | 0.04224 |
| 6.38 | 0.02632 | 0.02630 | 0.02581 |

Example 4

Pepsin and Proline-Specific Endopeptidase Digestion of Human Whole Blood Reduces Interference Caused by Hemoglobin S and Hemoglobin C When Calculating the Percentage of Glycated Hemoglobin: Proline-Specific Endopeptidase Digestion in the Presence of an Agglutinator Reagent Human whole blood samples containing Hemoglobin S (HbS) or Hemoglobin C (HbC) were tested in an agglutination inhibition immunoassay on an ADVIA® 1650 instrument as described in Example 2 to determine the concentration of glycated hemoglobin in the samples. The endopeptidase reagent contained approximately 6000 U/mL pepsin in 0.02 mol/L citrate buffer, pH 2.4, 0.2% Triton X100. The agglutinator reagent contained a mixture of approximately 1.5.mu.g/mL agglutinator (β-chain amino-terminal glycated sexapeptide of human hemoglobin conjugated to polyaspartamide) and increasing concentrations of proline-specific endopeptidase (0 U/mL, 0.1 U/mL, 0.2 U/mL, 0.33 U/mL, 0.43 U/mL and 0.54 U/mL) in a solution of 0.02 mol/L MOPS pH 7.0, 0.05% NaN.sub.3, 0.2% TWEEN®-20 detergent, 3 mmol/L EDTA, and 1.5% BSA.

The total hemoglobin concentration, which includes both glycated and non-glycated hemoglobin, in the samples was determined using the ADVIA® Total Hemoglobin Reagent (ADVIA® HbA1c reagent kit (Siemens Medical Solutions Diagnostics)) in an assay based on the conversion of all hemoglobin derivatives into alkaline hematin upon treatment with an alkaline solution of a nonionic detergent. Samples were added to the Total Hemoglobin Reagent and hemoglobin species were converted into alkaline hematin, which has a defined absorption spectrum at 596 nm. The hematin content was measured by determining absorption at 596 nm.

The percentage of glycated hemoglobin present in each sample was determined by dividing the concentration of glycated hemoglobin calculated for each sample by the concentration of total hemoglobin determined for the sample.

For comparative purposes, the percentage of glycated hemoglobin present in human whole blood samples containing hemoglobin S and hemoglobin C was also determined using the DCA® 2000 HbA1c assay (DCA® 2000 Analyzer and reagent kit (Siemens Medical Solutions Diagnostics)). The DCA® 2000 assay is known to have no interference from the presence of hemoglobin C and hemoglobin S variants. The percentage of glycated hemoglobin present in the samples was also determined using a standard HbA1c assay performed using the ADVIA® 1650 HbA1c method (Siemens Medical Solutions Diagnostics). The parameters listed in the Table 3 below were used on an ADVIA® 1650 instrument to evaluate the effect of proline-specific endopeptidase on hemoglobin variant interference. R1 was a mixture of the agglutinator (β-chain amino-terminal glycated sexapeptide of human hemoglobin conjugated to polyaspartamide) and 0.0-0.54 U/mL proline-specific endopeptidase in a solution of 0.02 mol/L MOPS pH 7.0, 0.05% $NaN_3$, 0.2% TWEEN®-20 detergent, 3.0 mmol/L EDTA, and 1.5% BSA. R2 was latex coated with mouse monoclonal anti-HbA1c antibody (ADVIA® HbA1c reagent kit, (Siemens Medical Solutions Diagnostics)).

TABLE 3

|  | Volume (μL) |
|---|---|
| R1 | 76 |
| R2 | 76 |
| Sample Pretreatment | 3.2 |
| Dilution | Special |
| Pepsin Reagent | 148 |
| Sample | 2 |
| Dil. Position | CTT |
| Assay type | 2PA |
| m | 56 |
| n | 72 |
| l | 0 |

TABLE 3-continued

|  | Volume (μL) |
|---|---|
| Wavelength | 694 nm |
| Calc. method | MSTD |
| Curve fit | Log-Logit 3 |

The results of the experiments are presented in Table 4 below. "NV" in the table indicates that a value was not obtained at that data point, and ">>>>" indicates that the value was too high for the instrument to measure. A "C" following the numerical designations in column 1 of the table indicates that the sample contains hemoglobin C, and an "S" following the numerical designations in column 1 indicates that the sample contains hemoglobin S. The results obtained with the HbA1c assay performed using the ADVIA® 1650 HbA1c method are greatly affected by the presence of hemoglobin S and hemoglobin C in the samples as compared to the results obtained with the DCA® 2000 HbA1c assay. Comparison of the results of experiments performed using differing proline-specific endopeptidase concentrations with the results of experiments performed using the DCA® 2000 HbA1c assay and using the ADVIA® 1650 instrument illustrates that interference in measurement of glycated hemoglobin caused by hemoglobin S and hemoglobin C is eliminated at a proline-specific endopeptidase concentration of 0.54 U/mL.

TABLE 4

| Sample | DCA | 0.0 U/mL PSE | 0.1 U/mL PSE | 0.2 U/mL PSE | 0.33 U/mL PSE | 0.43 U/mL PSE | 0.54 U/mL PSE | ADVIA 1650 |
|---|---|---|---|---|---|---|---|---|
| 6C | 8.7 | 11.97 | 10.56 | 10.09 | 9.44 | 8.97 | 8.72 | 11.88 |
| 14C | 6.8 | 8.26 | 7.74 | 7.09 | 6.93 | 6.95 | 6.56 | 8.07 |
| 18C | 7.4 | 8.63 | 8.44 | 8.50 | 8.40 | 7.86 | 7.94 | 7.97 |
| 42C | 6.2 | 7.61 | 7.02 | 6.65 | 6.47 | 6.37 | 6.10 | 7.67 |
| 46C | 6 | 6.90 | 6.55 | 6.39 | 6.12 | 6.10 | 5.83 | 6.90 |
| 47C | 6.5 | 8.03 | 7.10 | 6.92 | 6.59 | 6.70 | 6.33 | 7.79 |
| 64C | 9.3 | 12.67 | 11.44 | 10.84 | 10.29 | 9.85 | 9.53 | 15.07 |
| 97C | 5.5 | 8.37 | 7.91 | 7.46 | 7.17 | 6.83 | 6.62 | 8.44 |
| 126C | 8.6 | 12.47 | 11.58 | 10.92 | 10.20 | 9.42 | 9.42 | 13.08 |
| 187S | 6.8 | 7.42 | 7.02 | 6.73 | 6.62 | 6.77 | 6.74 | 7.92 |
| 188S | 6.1 | 7.41 | 6.82 | 6.46 | 6.43 | 6.17 | 6.12 | 7.41 |
| 191C | 6 | 7.76 | 7.34 | 6.80 | 6.72 | 6.39 | 6.12 | 7.83 |
| 192S | 6.5 | 7.69 | 7.17 | 6.81 | 6.58 | 6.29 | 6.08 | 7.75 |
| 213S | 6.4 | 7.44 | 6.93 | 6.52 | 6.26 | 6.09 | 5.96 | 7.62 |
| 214S | 5.6 | 7.18 | 6.43 | 6.16 | 5.87 | 5.68 | 5.64 | 7.07 |
| 215S | 6.1 | 7.87 | 7.34 | NV | 6.63 | 6.55 | 6.29 | 7.90 |
| 221S | 6.8 | 8.11 | 7.78 | 7.63 | 7.09 | 7.20 | 6.95 | 8.39 |
| 222C | 7.2 | 10.69 | 9.88 | 9.05 | 8.46 | 7.93 | 7.88 | 10.69 |
| 236C | 5.9 | 8.02 | 7.47 | 7.23 | 6.70 | 6.50 | 6.36 | 8.09 |
| 239S | 5.6 | 6.80 | 6.59 | 6.07 | 6.18 | 5.74 | 5.70 | 6.85 |
| 244S | 5.6 | 6.48 | 6.19 | 5.92 | 5.70 | 5.68 | 5.55 | 6.73 |
| 245C | 6.6 | 8.46 | 7.77 | 7.82 | 7.44 | 7.28 | 7.16 | 8.51 |
| 246S | 8.2 | 11.22 | 9.76 | 9.48 | 9.00 | 8.42 | 8.23 | 10.75 |
| 248S | 13 | 19.61 | 17.29 | 16.00 | 14.63 | 12.98 | 13.11 | >>>> |
| 251C | 5.9 | 7.22 | 6.91 | 6.62 | 6.46 | 6.31 | 6.07 | 7.37 |
| 252S | 6.2 | 7.41 | 6.91 | 6.56 | 6.46 | 6.26 | 6.26 | 7.47 |
| 253C | 6.3 | 8.72 | 8.43 | 7.59 | 7.24 | 7.07 | 6.79 | 8.76 |

The percentage of glycated hemoglobin present in the samples, as calculated from experiments performed with an ADVIA® 1650 instrument using the differing proline-specific endopeptidase concentrations (Table 4, columns 3 to 8) and performed using the ADVIA® 1650 HbA1c method (Table 4, column 9), were plotted against the glycated hemoglobin percentages calculated using the DCA® 2000 HbA1c assay (Table 4, column 2) to obtain correlation slopes for the glycated hemoglobin percentages calculated at each proline-specific endopeptidase concentration and for the percentages calculated using the ADVIA® 1650 HbA1c method. The results are shown in FIGS. 3 to 9, which indicate that as the proline-specific endopeptidase concentration increased, interference in calculating the percentage of glycated hemoglobin present in the samples caused by hemoglobin S and hemoglobin C decreased until it was eliminated.

Figure 10:
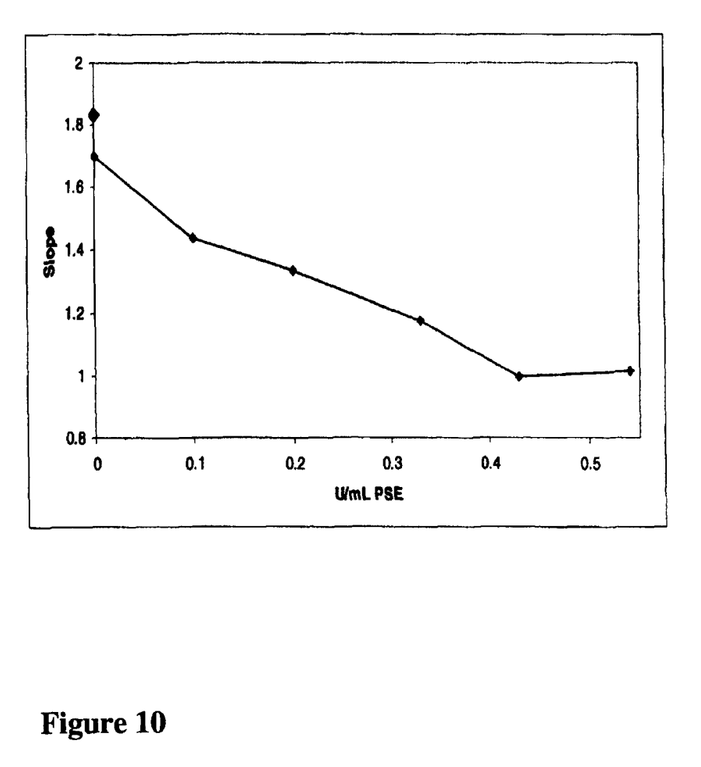
FIG. 10 depicts values of the correlation slopes illustrated in FIGS. 3 to 9 plotted against proline-specific endopeptidase concentration.

The values of the correlation slopes determined as described in the preceding paragraph and illustrated in FIGS. 3 to 9 were plotted against the proline-specific endopeptidase concentration (FIG. 10), demonstrating that digestion of human whole blood samples containing hemoglobin S and hemoglobin C with pepsin followed by digestion with at least 0.43 U/mL proline-specific endopeptidase in the presence of an agglutinator reagent eliminates interference caused by hemoglobin S and hemoglobin C when calculating the percentage of glycated hemoglobin present in the samples.

Example 5

Pepsin and Proline-Specific Endopeptidase Digestion of Human Whole Blood Reduces Interference Caused by Hemoglobin S and Hemoglobin C When Calculating the Percentage of Glycated Hemoglobin: Pepsin Digestion in the Presence of an Agglutinator Reagent Human whole blood samples containing hemoglobin S and hemoglobin C were diluted with saline solution on an ADVIA 1650 instrument using the parameters listed in table 5.

TABLE 5

|  | Volume (μL) |
| --- | --- |
| R1 | 76 |
| R2 | 76 |
| Sample Pretreatment | 3.2 |
| Dilution | Special |
| Saline | 148 |
| Sample | 2 |
| Dil. Position | CTT |
| Assay type | 2PA |
| m | 56 |
| n | 72 |
| l | 0 |
| Wavelength | 694 nm |
| Calc. method | MSTD |
| Curve fit | Log-Logit 3 |

The saline-diluted samples were then mixed with an agglutinator reagent containing approximately 1.5 μg agglutinator (β-chain amino-terminal glycated sexapeptide of human hemoglobin conjugated to polyaspartamide) and 6 U/mL pepsin in 0.02 mol/L citrate buffer, pH 2.4, and the mixture was incubated for five minutes. Solutions of latex coated with mouse monoclonal anti-HbA1c antibody (ADVIA® HbA1c reagent kit, (Siemens Medical Solutions Diagnostics)) containing increasing concentrations of proline-specific endopeptidase (0.0, 1.0, 2.0, 3.0, 4.0, or 5.0 U/mL) (pH 7) were then added to the agglutinator reagent/pepsin solution and the mixture was incubated for five minutes. Agglutination rates at 694 nm were determined using an ADVIA® 1650 instrument, and the agglutination rates were used to calculate the concentration of glycated hemoglobin S or hemoglobin C in the samples.

For comparative purposes, the percentage of glycated hemoglobin present in the samples was also determined using the DCA® 2000 HbA1c assay (DCA 2000® Analyzer and reagent kit (Siemens Medical Solutions Diagnostics)).

The total hemoglobin concentration in the samples was determined according to the procedures described in Example 4, and the percentage of glycated hemoglobin present in each sample was also determined as described in Example 4. The results of the experiments are presented in Table 6 below and indicate that digestion of human whole blood samples with pepsin in the presence of an agglutinator reagent followed by digestion with proline-specific endopeptidase significantly reduces interference caused by hemoglobin S and hemoglobin C present in the samples when calculating the percentage of glycated hemoglobin present in the samples.

TABLE 6

| | U/mL PSE | | | | | | |
| --- | --- | --- | --- | --- | --- | --- | --- |
| Sample ID | 0 U/mL | 1 U/mL | 2 U/mL | 3 U/mL | 4 U/mL | 5 U/mL | DCA |
| | % Glycated Hb | | | | | | |
| 185S | 10.36 | 10.95 | 9.71 | 8.89 | 8.65 | 8.55 | 10.1 |
| 180C | 6.25 | 5.93 | 5.54 | 5.29 | 5.14 | 5.10 | 5.6 |
| 22C | 13.72 | 11.33 | 10.72 | 9.42 | 9.00 | 8.61 | 9.12 |
| 172S | 12.22 | 11.03 | 10.43 | 9.86 | 9.53 | 9.00 | 10.6 |

The entire disclosure of each patent, patent application, and publication cited or described in this document is hereby incorporated herein by reference.

We claim:

1. A method for detecting glycated human hemoglobin comprising:
    contacting a blood sample to be tested for glycated human hemoglobin with an endopeptidase;
    contacting the endopeptidase-treated blood sample with proline-specific endopeptidase;
    and detecting glycated β-chain amino-terminal pentapeptide of human hemoglobin.

2. The method of claim 1 wherein the blood sample is human whole blood.

3. The method of claim 1 comprising determining the percentage of glycated human hemoglobin in the sample.

4. The method of claim 1 wherein the endopeptidase is an acid endopeptidase selected from the group consisting of pepsin, aspergillopepsin II, cathepsin D, saccharopepsin, mucorpepsin, chymosin, gastricsin, and physirolisin.

5. The method of claim 4 wherein the acid endopeptidase is pepsin.

6. The method of claim 5 comprising contacting the sample with about 5 U/mL to about 10,000 U/mL pepsin at a pH in the range of about 1.0 to about 5.0.

7. The method of claim 1 comprising contacting the endopeptidase-treated blood sample with about 0.1 U/mL to about 30 U/mL proline specific endopeptidase at a pH in the range of about 5.0 to about 9.0.

8. The method of claim 1 comprising detecting the glycated β-chain amino-terminal pentapeptide of human hemoglobin with a method that comprises the use of high performance liquid chromatography or that comprises the binding of at least one antibody to the glycated pentapeptide.

9. The method of claim 1 comprising detecting the glycated β-chain amino-terminal pentapeptide of human hemoglobin with an agglutination inhibition immunoassay.

10. The method of claim 9 wherein the agglutinator reagent used in the agglutination inhibition immunoassay is a glycated val-his-leu-thr-tyr-cys (SEQ ID NO: 4) sexapeptide conjugated to polyaspartamide.

11. The method of claim 9 comprising contacting the endopeptidase-treated blood sample with proline specific endopeptidase either simultaneously with, prior to, or following contacting the blood sample with an agglutinator reagent.

12. The method of claim 11 comprising contacting the endopeptidase-treated blood sample with a mixture of proline specific endopeptidase and the agglutinator reagent.

13. The method of claim 12 wherein the mixture of proline specific endopeptidase and the agglutinator reagent comprises about 0.1 g/dL to about 5.0 g/dL bovine serum albumin and about 0.5 mmol/L to about 10.0 mmol/L ethylenediamine tetraacetic acid and has a pH in the range of about 6.0 to about 8.0.

14. The method of claim 11 further comprising contacting the endopeptidase, proline specific endopeptidase, and agglutinator reagent-treated blood sample with an antibody that specifically binds to both glycated β-chain amino-terminal pentapeptide of human hemoglobin and the agglutinator reagent.

15. The method of claim 14 wherein at least one antibody molecule is bound to one or more latex particles.

16. A method for detecting glycated human hemoglobin comprising: contacting a blood sample to be tested for glycated human hemoglobin with an endopeptidase either simultaneously with, prior to, or following contacting the blood sample with an agglutinator reagent; contacting the endopeptidase and agglutinator reagent-treated blood sample with proline-specific endopeptidase; and detecting glycated β-chain amino-terminal pentapeptide of human hemoglobin with an agglutination inhibition immunoassay.

17. The method of claim 16 wherein the endopeptidase is an acid endopeptidase selected from the group consisting of pepsin, aspergillopepsin II, cathepsin D, saccharopepsin, mucorpepsin, chymosin, gastricsin, or physirolisin.

18. The method of claim 17 wherein the acid endopeptidase is pepsin.

19. The method of claim 18 comprising contacting the sample with a mixture of pepsin and the agglutinator reagent.

20. The method of claim 19 wherein the mixture of pepsin and the agglutinator reagent comprises about 3 U/mL to about 100 U/mL pepsin and has a pH in the range of about 1.0 to about 4.0.

21. The method of claim 16 further comprising contacting the endopeptidase and agglutinator reagent-treated blood sample with proline specific endopeptidase either simultaneously with or before contacting the blood sample with an antibody that specifically binds to both glycated β-chain amino-terminal pentapeptide of human hemoglobin and the agglutinator reagent.

22. The method of claim 21 comprising contacting the endopeptidase and agglutinator reagent-treated blood sample with a mixture of proline specific endopeptidase and the antibody.

23. The method of claim 22 wherein the mixture comprises about 2.0 U/mL to about 30.0 U/mL proline specific endopeptidase and has a pH in the range of about 7.0 to about 8.0.

24. The method of claim 21 wherein at least one antibody molecule is bound to one or more latex particles.

* * * * *